US00PP12053P2

(12) United States Plant Patent
Shiigi

(10) Patent No.: US PP12,053 P2
(45) Date of Patent: Aug. 14, 2001

(54) GUZMANIA PLANT NAMED 'ALII'

(76) Inventor: David Shiigi, 35 Pau-O-Palae St., Hilo, HI (US) 96720

( * ) Notice: Subject to any disclaimer, the term of this patent is extended or adjusted under 35 U.S.C. 154(b) by 0 days.

(21) Appl. No.: 09/240,798

(22) Filed: Jan. 26, 1999

(51) Int. Cl.[7] ..... A01H 5/00
(52) U.S. Cl. ..... Plt./371
(58) Field of Search ..... Plt./371

(56) References Cited

U.S. PATENT DOCUMENTS

P.P. 9,768 * 12/1996 Shiigi ..... Plt./371

* cited by examiner

*Primary Examiner*—Bruce R. Campell
*Assistant Examiner*—Kent L. Bell
(74) *Attorney, Agent, or Firm*—Laubscher & Laubscher

(57) ABSTRACT

There is disclosed a hybrid Guzmania obtained from crossing *G. 'Memoria'* and *G. 'Insignis'*, which possesses a distinctive brilliant yellow inflorescence rising above the red and green foliage on a scape bearing leaf-like bracts red and green in color, which inflorescence retains conspicuous coloration for up to four months.

2 Drawing Sheets

BACKGROUND OF THE INVENTION

The present invention is a new and distinct Guzmania hybrid, *Guzmania 'Memoria'*×*Guzmania 'Insignis'*, of the Bromeliad family. The pollen parent, *G. 'Memoria'* (unpatented), is a cultivar of *Guzmania lingulata*. The seed parent, *G. 'Insignis'* (unpatented), is a hybrid of *G. lingulata v. splendens* and *G. zahnii.*

From this cross numerous seedlings were raised, displaying variable characteristics. These seedlings were separated into groups for purposes of identifying and isolating plants having characteristics deemed worthy of preservation. Many of the seedlings were raised to maturity. From among these, I have discovered plants substantially different from one another and Guzmania varieties known to me. The present invention is a plant from this cross which I isolated from the others due to it having the unique combination of a yellow inflorescence and red scape (basal) bracts. I have asexually reproduced the plant by removal of vegetative offshoots, and have found that the plant retains its distinctive characteristics and reproduces true to type through successive generations of asexual reproduction. I first asexually reproduced the plant in the mid-1980s at the shadehouse facility I then possessed in the town of Pahoa in Puna District on the island of Hawaii, and have since asexually reproduced the plant at my present growing facilities in Hilo, Hi.

*Guzmania 'Alii'* is readily distinguished from its parent cultivars. The following comparative descriptions are based on plants grown under similar conditions in Hawaii. Plants were grown in 73% to 80% shade at temperatures of 78° to 90° F. during the summer and 68° to 80° F. during the winter, and were watered and fertilized on a regular basis.

The pollen plant, *G. 'Memoria'*, is of medium size and ranges from 60 to 68 centimeters (cm) in diameter producing 30 to 35 leaves. The plant rises to a height of 20 to 28 cm without inflorescence. When in bloom, the inflorescence rises from the center of the plant giving the plant an overall height of 32 to 40 cm. The basal leaves range in length from 38 to 42 cm. The leaves are 5 to 6 cm wide beginning at the base and extending 8 to 10 cm from the base tapering to a width of 3 to 3.5 cm for a majority of the remainder of its length terminating in a tip 2 cm wide and 3 cm long. There are approximately 13 to 16 bracts that form a 14 to 19 cm diameter star when viewed from above. Each bract ranges in length from 2 to 2.5 cm having a width of 4 to 5 cm at its widest point tapering to 2.5 to 3 cm at midpoint, and terminating in a tip 2 to 2.5 cm in width. The bracts are red-orange (RHS45D) in color and the inner floral cone is yellow-orange (RHS24B) with white tips.

The seed plant, *G. 'Insignis'*, is a hybrid of *G. lingulata v. splendens* and *G. zahnii. G. 'Insignis'* is a medium to large size plant with a diameter ranging from 83 to 88 cm with a height ranging from 82 to 87 cm. The basal leaves range in length from 50 to 56 cm and have a width ranging from 6 to 7 cm from the base extending from the base approximately 14 to 16 cm tapering to 2 to 3.5 cm for a majority of the remainder of its length terminating in a tip 2 cm in width. The leaves have fine red stripes emanating from the base which fade at a point approximately 15 to 17 cm from the base of the leaves. The inflorescence is composed of a bract cluster containing about 16 to 20 bracts, which range from 10 cm to 15 cm in diameter. The cluster forms a star shape when viewed from above. The bracts are red (RHS43B). The inner floral cones are yellow (RHS1B), with the lower most segments (which are not visible unless the inflorescence is dissected) being tinged with reddish striations.

*Guzmania 'Alii'* combines the characteristics of its parents in a unique manner. It is nearly the same size in diameter as *G. 'Insignis'*, being approximately 80 to 86 cm in diameter compared to 83 to 88 cm for *G. 'Insignis'*, but reaches a height intermediate between its parents of 54 to 56 cm, compared to 82 to 87 cm for *G. 'Insignis'* and 32 to 40 cm for *G. 'Memoria'*. The leaves of *G. 'Alii'* are approximately as long as those of *G. 'Insignis'*, but the width is more similar to the width of the leaves of *G. 'Memoria'*. The basal leaves of *G. 'Alii'* are approximately 56 to 60 cm long, compared to *G. 'Memoria'* having basal leaves 38 to 42 cm in length and *G. 'Insignis'* having basal leaves 50 to 56 cm in length. The width of the leaves of *G. 'Alii'* at their widest point at the base of the oldest leaves is 5 to 6.5 cm, compared to 5 to 6 cm for *G. 'Memoria'* and 6 to 7 cm for *G. 'Insignis'*. The inflorescence of *G. 'Alii'* is composed of 20 to 23 bracts, compared to 13 to 16 bracts for *G. 'Memoria'* and 16 to 20 bracts for *G. 'Insignis'*. Both the outer and inner floral bracts of *G. 'Alii'* are brilliant yellow, held on a scape bearing red suffused leaf-like bracts. The predominate inflorescence color of *G. 'Alii'* is a brilliant yellow contrasting with leaf-like scape bracts of red and green. In comparison, for *G. 'Memoria'* the predominate color is a bright red-orange, and for *G. 'Insignis'* the inflorescence coloration is composed equally of deep red outer floral bracts and bright yellow cone-shaped inner floral bracts, held on a scape bearing reddish leaf-like scape bracts.

DETAILED DESCRIPTION OF THE INVENTION

Figure 1:
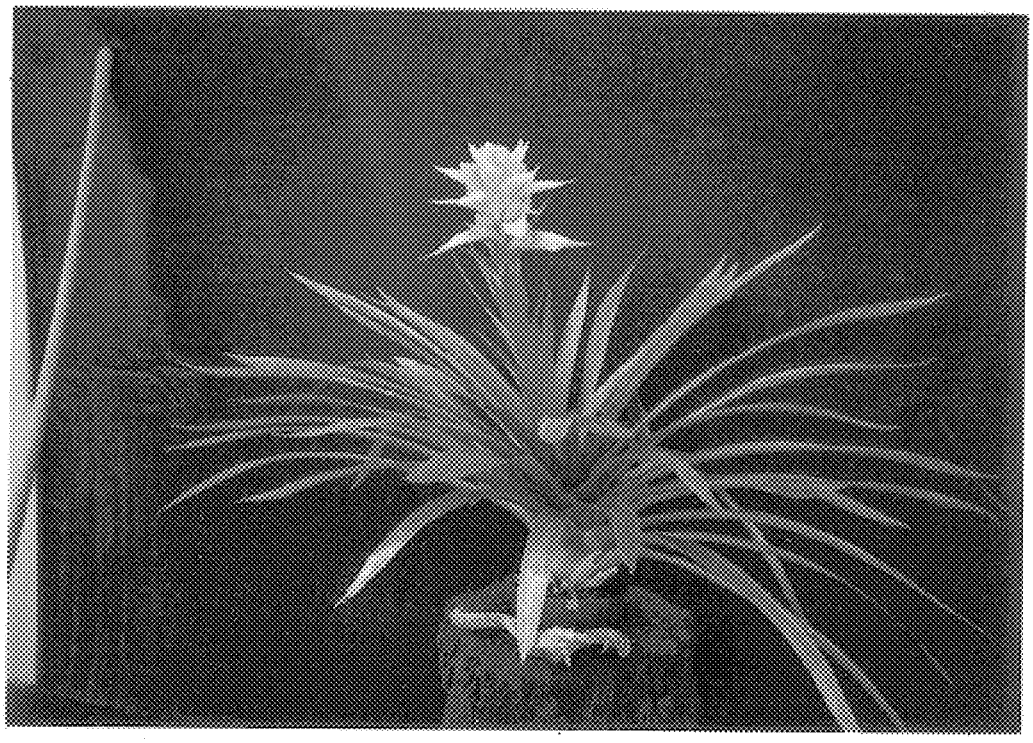
FIG. 1 is a photograph of a typical plant of *G. 'Alii'* in bloom.
Figure 2:
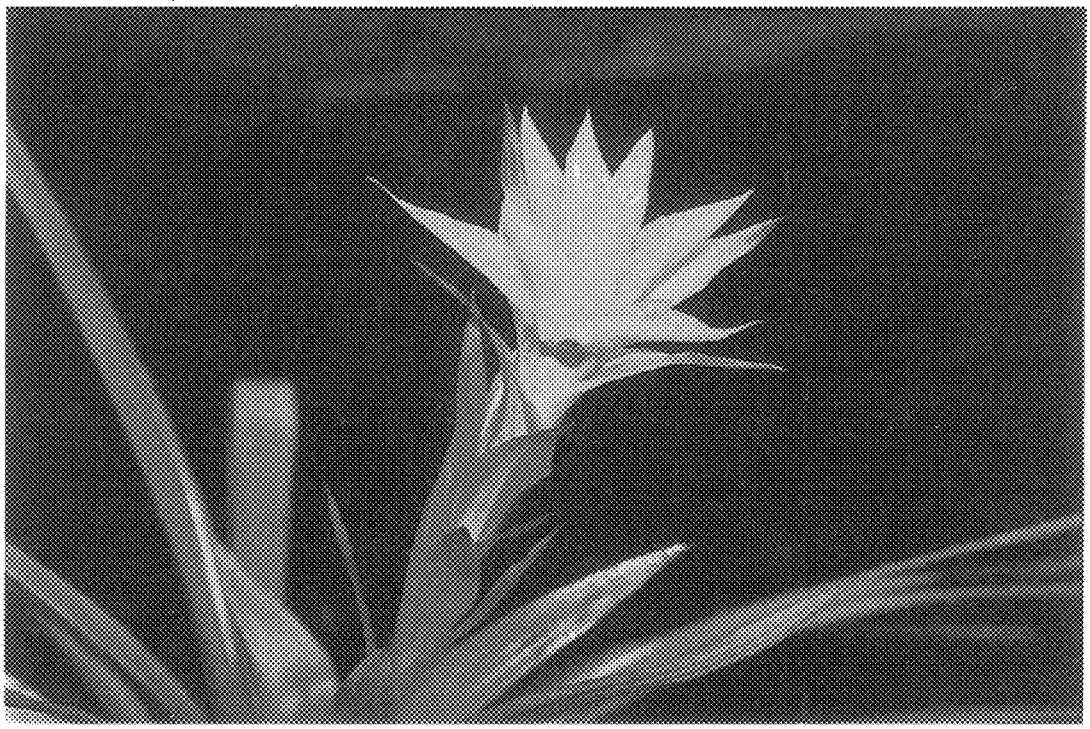
FIG. 2 is a photograph of the inflorescence viewed from the side.
Figure 3:
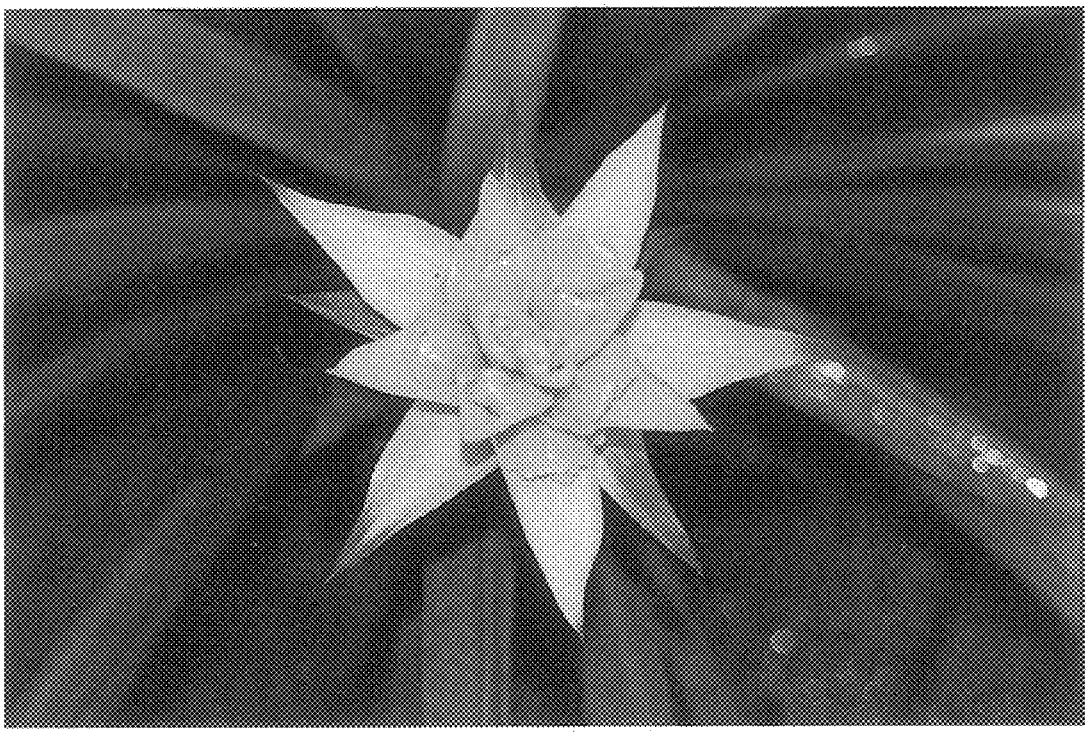
FIG. 3 is a photograph of the inflorescence viewed from above showing the star shape formed by the bracts and the red tinged bract tips.

The following is a detailed description of my new variety, based on observations of mature blooming plants approximately 14 months of age (from time of potting a 6-inch offset). These were grown in shadehouse facilities in Hilo, Hi. The ambient temperature generally ranged between 78° to 90° F. during the summer and between 68° to 80° F. during the winter, with temperatures rising as high as 100° F. in enclosed areas for short intervals on occasion during the summer and reaching lows of 60° for short intervals on occasion during the winter. Natural sunlight intensity was controlled by use of shade cloth and shading compounds to create 73%–80% shade. Irrigation occurred as needed to maintain moist potting media, with fertilizer being applied in liquid solution approximately monthly. Color references are made to The Royal Horticultural Society Colour Chart ("R.H.S.") followed by the number and letter designating the specific color.

PLANT

I. Parentage: *Guzmania 'Memoria'*×*Guzmania 'Insignis'*.

II. Propagation: Retains its distinctive characteristics through successive generations of asexual reproduction. Successful reproduction has been accomplished by removal of offsets.

III. Form: The plant forms an upright, spreading, open vase shape.

IV. Growth: A moderately fast-growing plant with a rate of growth similar to other hybrids of *Guzmania lingulata* known to me. When grown utilizing a comprehensive feeding program with weekly application of dilute liquid fertilizer, a 6-inch offset can be raised to mature size in 9–12 months. My new variety neither suffers any known susceptibility to insects or plant pathogens, nor enjoys any known resistance to same, compared to other *G. lingulata* hybrids known to me.

LEAVES

The leaves range from green (RHS 144A) with red RHS46B striations to solid dark red RHS46A at their base, becoming medium green (RHS144A) at a point approximately ½ to ⅔ of the length of the leaf measured from the base. Both abaxial and adaxial sides are of the same color. Leaves are linear, with the leaf tip acute and the margin smooth. The oldest outer leaves are approximately 56 to 60 cm in length. The leaves have a width of approximately 5 to 6.5 cm at their base, narrowing to a width of 4.5 to 4.0 cm at a distance of 13 cm from the leaf base, and gradually tapering to an acute tip. Each emerging leaf is gradually shorter than the last. The plant produces approximately 36 to 40 leaves.

INFLORESCENCE

The inflorescence is composed of bracts arranged radially at the top of a stem (scape) which rises from the center of the plant, with the radial formation of the primary bracts forming a star shape when viewed from above, and the overall inflorescence having a torch shape when viewed from the side. The primary bracts spread open, exposing cone-shaped floral bracts from which individual flowers emerge. The cone-shaped floral bracts are closely affixed to the scape at the upper base of the primary bracts. The scape rises above the height of the foliage and bears scape bracts (or basal bracts) which are leaf-like in appearance. The inflorescence blooms for 2–3 months, and retains its conspicuous color for up to 4 months. The detail description of the floral parts is as follows:

I. Bracts

- *A. Primary bracts.*—Number — 22–25. Shape — Apiculate. Margin — Entire, smooth. Length — 8–12 cm. Width — Approximately 3.5 cm at base, tapering to acute tip. Color — Yellow (RHS8A), with lower-most bracts having reddish striations (RHS46B). The very tip of some bracts is often tinged red (RHS44C). (Color designations represent both upper and lower surfaces).
- *B. Floral bracts.*—Number — 21 to 24. Shape — Conical. Margin — Entire, smooth. Apex — Acute. Length — 2.5 to 3.0 cm. Width — 2.5 to 4.5 cm. Color — yellow (RHS17B) (Both upper and lower surfaces).
- *C. Scape bracts.*—Shape — Lanceolate. Margin — Entire, smooth. Apex — Acute. Length — lowermost are 27–34 cm in length, becoming progressively shorter until only 11–16 cm in length immediately below the primary bracts. Color — Red (RHS46B) at the base where affixed to the scape, becoming light green (RHS144A) at the tip. (Color designations represent both upper and lower surfaces).

II. Flower:

- *Color.*—Pale yellow (RHS8C) (Both surfaces).
- *Corolla.*—Cylindrical, 1.5 cm in length at anthesis.
- *Sepals.*—3 in number, pale yellow (RHS8C) (Both surfaces) in color, 0.5 cm wide, 3 cm long.
- *Petals.*—3 in number, pale yellow (RHS8C) (Both surfaces) in color, ranging from 2 to 3 mm in width and 1 cm in length.
- *Pistil.*—1 in number.
- *Stamens.*—6 in number (occasionally defective with only 5), ranging in length from 1 to 1.5 cm.
- *Stigma.*—1.5 cm in length.
- *Number.*—Approximately 280 to 300 flowers emerge from the floral bracts over a period of months, but rarely open.

III. Seed/fruit: None observed. Over the course of several years working with my new invention, no pollination has occurred. The flowers do not open, with rare exception. The stigma has not been observed to develop the stickiness characteristic of Guzmania, and pollen is not produced.

I claim:

1. A new and distinct variety of Guzmania plant, as herein illustrated and described.

* * * * *